US012414831B1

(12) United States Patent
Arsenault

(10) Patent No.: US 12,414,831 B1
(45) Date of Patent: Sep. 16, 2025

(54) SINGULARIZING ACCESSORY ATTACHABLE TO A DISPOSABLE GLOVE DISPENSER

(71) Applicant: Peter Arsenault, Dracut, MA (US)

(72) Inventor: Peter Arsenault, Dracut, MA (US)

( * ) Notice: Subject to any disclaimer, the term of this patent is extended or adjusted under 35 U.S.C. 154(b) by 0 days.

(21) Appl. No.: 18/909,518

(22) Filed: Oct. 8, 2024

(51) Int. Cl.
*A61B 42/40* (2016.01)

(52) U.S. Cl.
CPC ................ *A61B 42/40* (2016.02)

(58) Field of Classification Search
CPC ..................................... A61B 42/40
USPC ..................................... 221/33–63
See application file for complete search history.

(56) References Cited

U.S. PATENT DOCUMENTS

| | | | | |
|---|---|---|---|---|
| 5,647,506 | A * | 7/1997 | Julius ............... | A47K 10/421 206/449 |
| 7,600,641 | B2 * | 10/2009 | Burgess ............ | B65H 19/18 383/66 |
| 9,327,892 | B2 * | 5/2016 | Rubo ................ | B65D 75/5838 |
| 10,959,799 | B2 * | 3/2021 | Quintana ........... | A61B 42/40 |
| 2008/0314920 | A1 * | 12/2008 | Rodrigues ......... | A61B 50/20 221/63 |
| 2012/0145737 | A1 * | 6/2012 | Ray ................... | B65D 83/0805 221/45 |
| 2014/0021215 | A1 * | 1/2014 | Tran .................. | B65H 1/08 221/45 |
| 2014/0367400 | A1 * | 12/2014 | Crudge .............. | A47K 10/38 221/63 |
| 2015/0272405 | A1 * | 10/2015 | Powling ............. | A47K 10/421 221/63 |
| 2016/0088980 | A1 * | 3/2016 | BenMark Markovitch ....... | A47K 10/42 221/45 |
| 2016/0368690 | A1 * | 12/2016 | Yokoyama ........ | B65D 75/5838 |

* cited by examiner

*Primary Examiner* — Gene O Crawford
*Assistant Examiner* — Ayodeji T Ojofeitimi
(74) *Attorney, Agent, or Firm* — Onello & Mello P.C.

(57) ABSTRACT

An accessory attachable to a glove dispensing box singularizes dispensing of gloves therefrom. The accessory includes a frangible cover comprising a longitudinal slit or perforation positioned over a dispensing region of the box. As a selected glove is removed, sides of the opened longitudinal slit or perforation exert a frictional resistance that scrapes away and prevents dispensing of additional gloves that may have mutually attached themselves to the selected glove. The frangible cover can be approximately rectangular and comprise a single longitudinal perforation or slit, or a round or square cover comprising a plurality of radially extending slits or perforations. The frangible cover can be attachable by an adhesive, or a sleeve into which the box is removably inserted. An orthogonal slit or perforation transverse to the longitudinal slit or perforation can enhance access to the box interior. The frangible cover can be at least 0.003 inches thick.

13 Claims, 16 Drawing Sheets

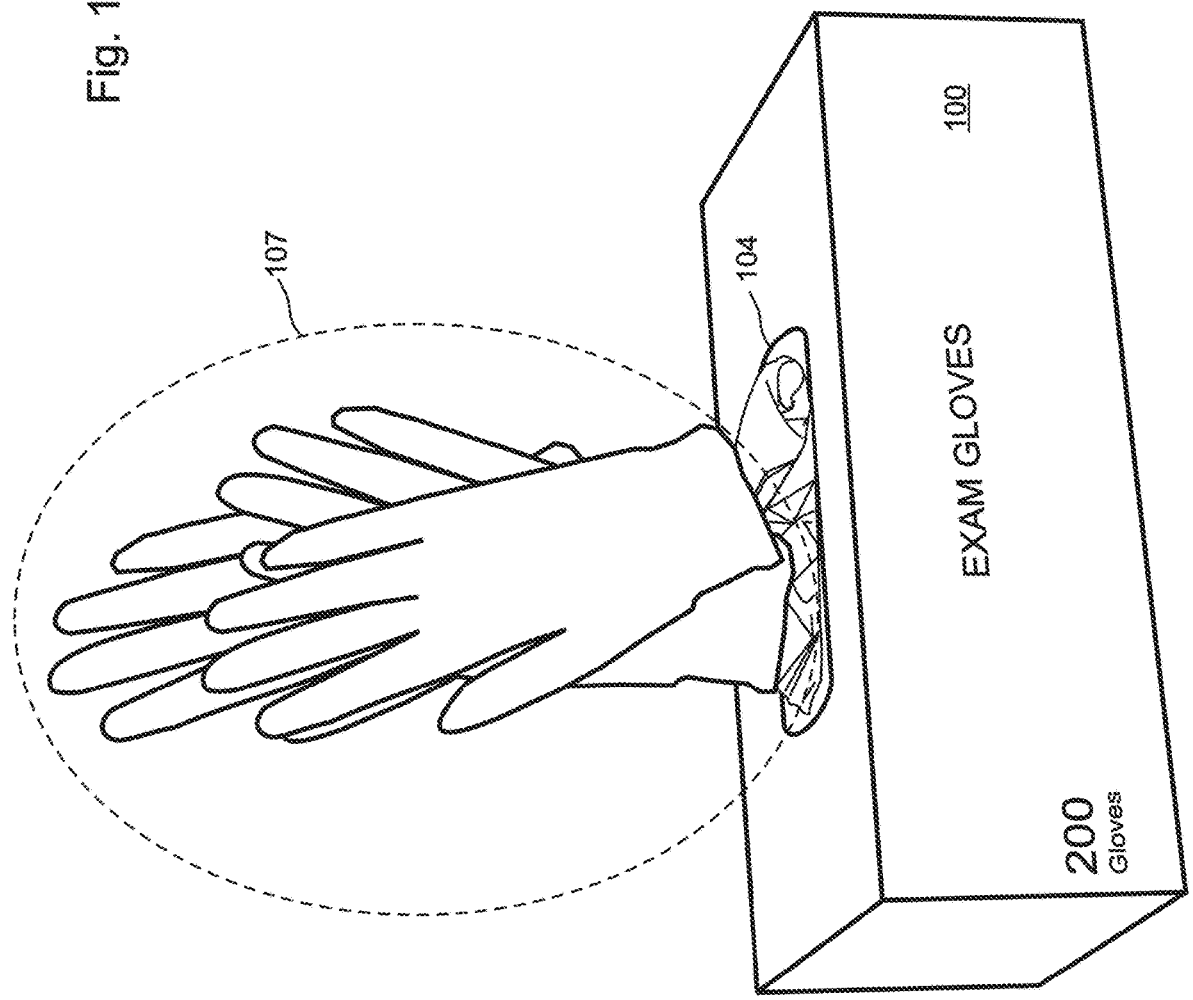

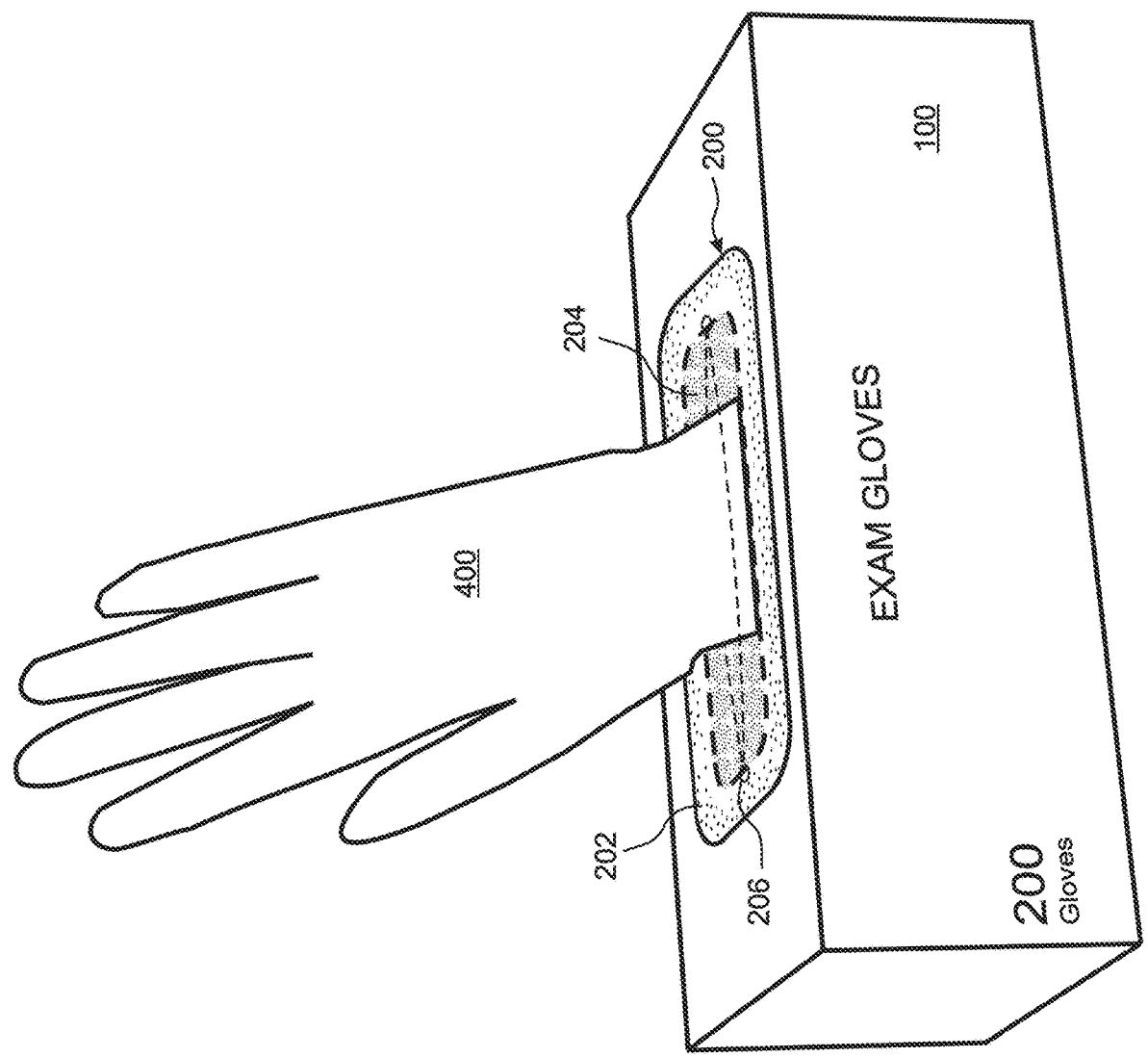

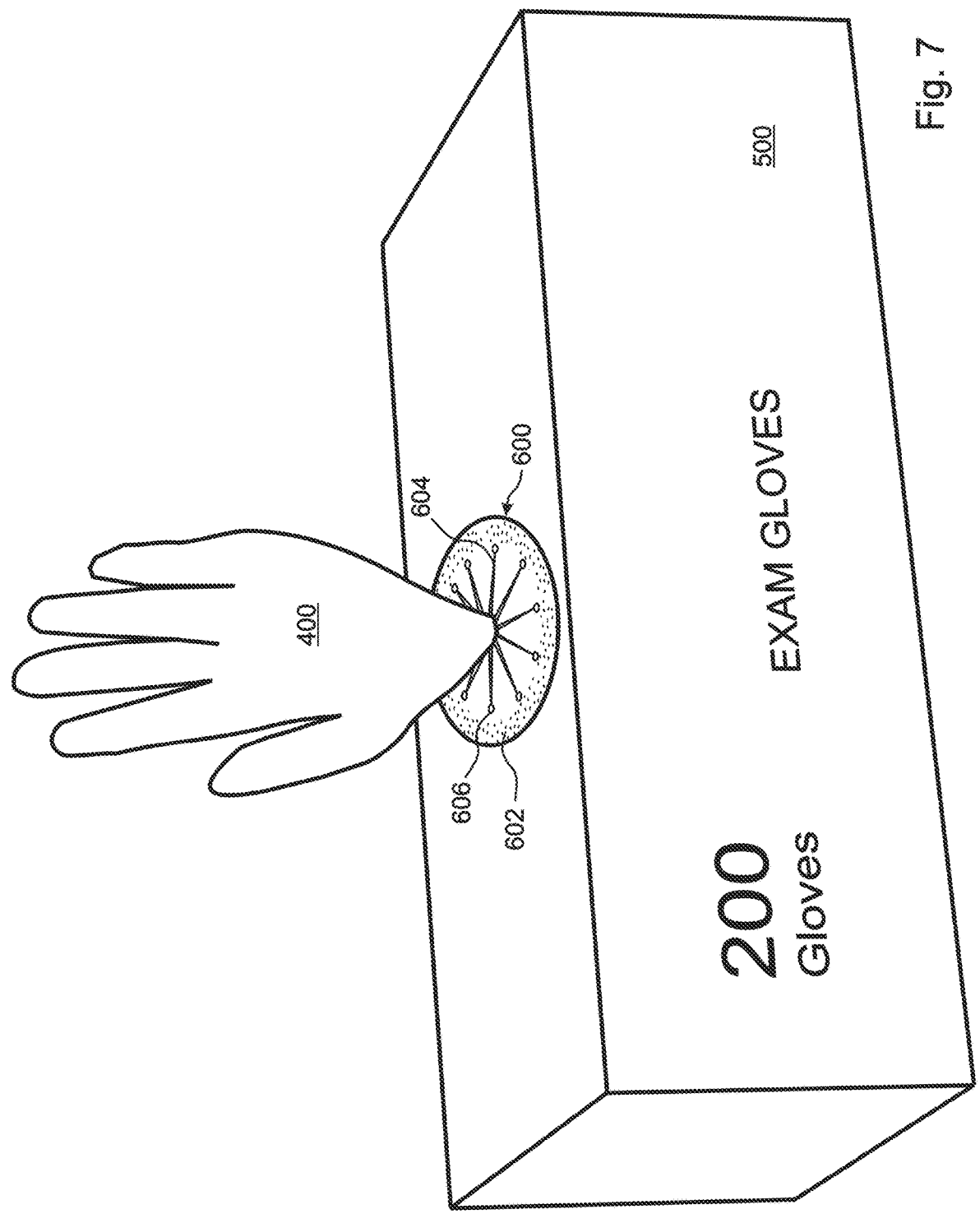

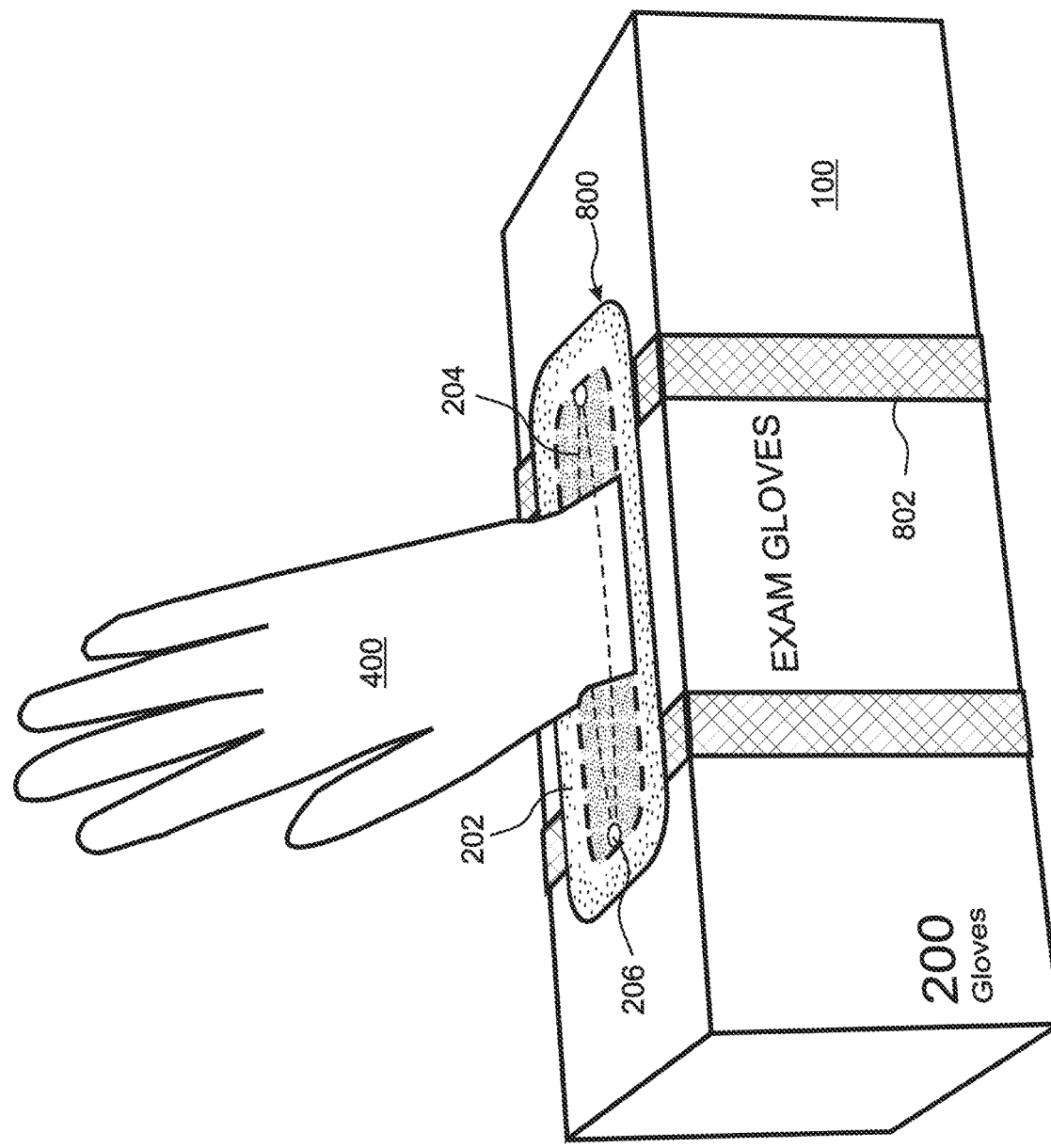

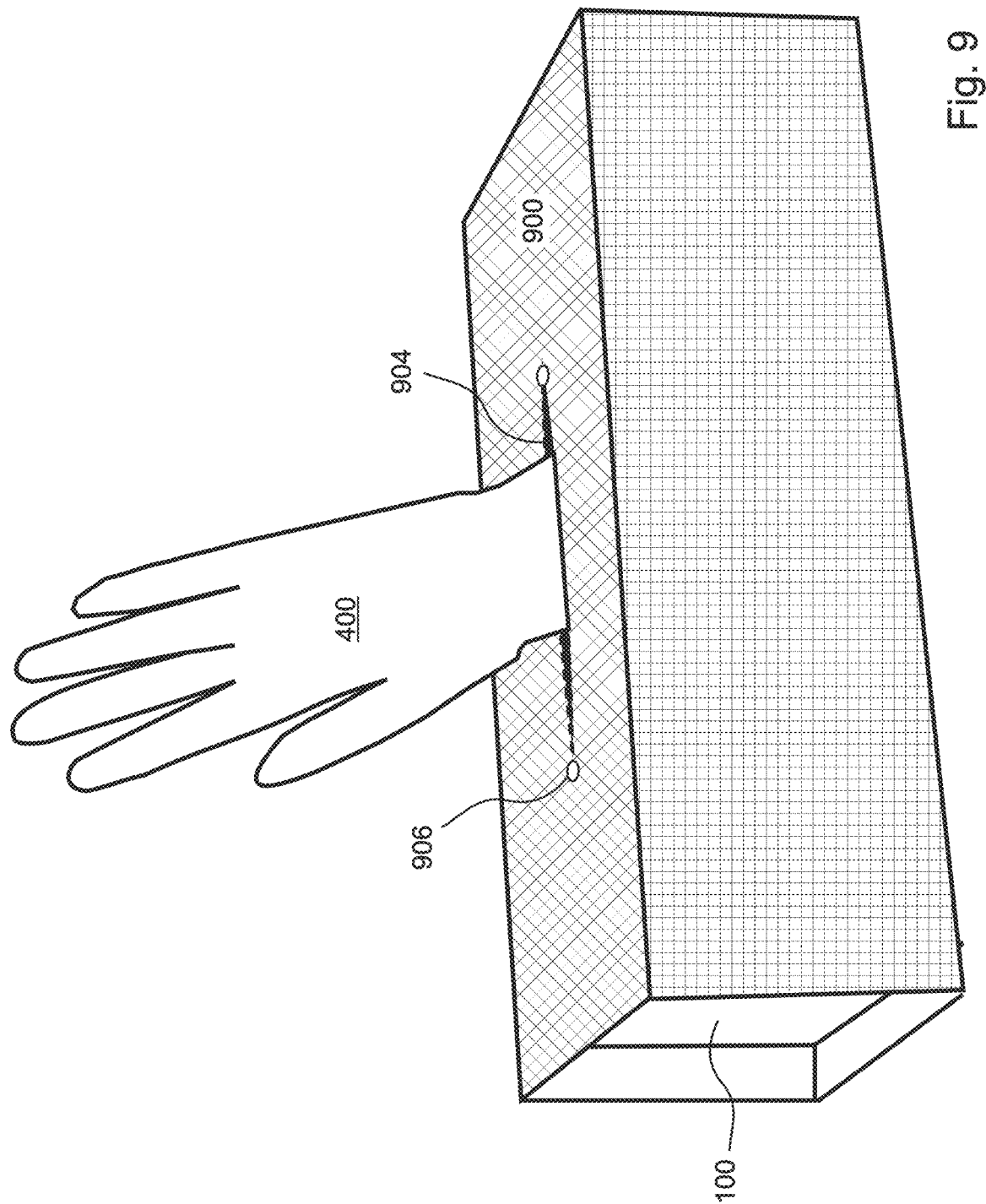

SINGULARIZING ACCESSORY ATTACHABLE TO A DISPOSABLE GLOVE DISPENSER

FIELD OF THE INVENTION

The invention relates to glove dispensers, and more particularly, to apparatus and methods for singularizing the dispensing of disposable gloves.

BACKGROUND OF THE INVENTION

Disposable gloves are widely used in the medical and dental fields for routine examinations, surgeries, and other examinations and treatments where manual contact with patients is required. Typically, such gloves are made from elastomeric materials such as latex, nitrile rubber, polyvinyl chloride, and neoprene.

Normally, with reference to FIG. 1A, disposable medical gloves are supplied in tightly packed glove dispensing boxes 100, which include a dispensing region 102 on an upward-facing surface 103. The dispensing region 102 is initially covered by a cover panel of box material that is surrounded and defined by a frangible, perforated circumference 104. Most commonly, the box 100 is made from cardboard, which is inexpensive, recyclable, and easily perforated.

This form of packaging allows the contents of the glove dispensing box 100 to remain clean while the glove dispensing box 100 is being stored. With reference to FIG. 1B, when access to the contents of the glove dispensing box 100 is required, the cover panel is removed from the dispensing region 102 by breaking the perforated circumference 104. A user is then able to reach into the box 100 through the dispensing region 104, grasp one of the contained gloves 106, and pull it upward through the dispensing region, which is now a dispensing opening.

Unfortunately, with reference to FIG. 1C, it can be difficult for a user to grasp only a single glove. And even if the user does manage to grasp only one glove, it is likely that additional gloves will adhere to the selected glove due to the inherent mutual adhesion of the elastomeric glove material. As a result, an attempt to remove a single glove is likely to result in a plurality of gloves 107 emerging from the box 100, some of which will likely fall onto surrounding furniture or onto the floor. This result is at least inconvenient. And if it is necessary for the gloves to remain clean, then it may be necessary to repurpose or dispose of any additional, unwanted gloves 107 that are removed from the box 100, which is wasteful and costly.

With reference to FIG. 1D, one approach that has been attempted for glove dispensing boxes is to package the disposable gloves in a box 110 that would normally be used for dispensing facial tissues 118. Cost is minimized by applying appropriate graphics to an otherwise unmodified tissue box 110, thereby avoiding most of the cost that would be associated with designing a box specifically for dispensing disposable gloves.

Typically, the dispensing region 112 of a tissue dispensing box 110 is covered by a clear plastic layer 114 in which a central, longitudinal perforation 116 is provided. In most cases, the clear plastic layer 114 is applied to the lid of the dispensing box 110 from below. With reference to FIG. 1E, once the longitudinal perforation 116 is broken, a user is able to grasp the uppermost tissue 118 and withdraw it from the box 110. Typically, the tissues are inter-folded, so that when the selected tissue 118 is removed from the box 110, a next uppermost tissue is pulled partially out through the longitudinal perforation 116 of the plastic layer 114.

Unlike disposable gloves, tissues do not tend to mutually adhere to each other, due to the non-elastic nature of the paper from which they are made. As a result, the clear plastic layer 114 of a tissue dispensing box 110 plays little if any role in preventing unwanted dispensing of additional tissues. Instead, the clear plastic layer 114 of a tissue dispensing box 110 is provided mainly to prevent unwanted dust and other detritus from falling into the tissue box 110 through the dispensing region 112. Also, when the next uppermost tissue is pulled partially out through the longitudinal perforation 116 of the plastic layer 114 due to the interfolding of the tissues 118, the next-uppermost tissue is grasped and held in place by edges of the opened longitudinal perforation 116, so that the next-uppermost tissue can be easily grasped by a user at a later time.

Unfortunately, this approach has met with limited success when applied to glove dispensing boxes, because the thin plastic layer of transparent plastic 114 is not strong enough to "singularize" the gloves 107, and fails to reliably limit the gloves 107 to being dispensed one at a time. This is mainly due to the mutual adherence of the gloves 107 to each other, which does not occur with facial tissues. Furthermore, as the gloves are dispensed, there is a tendency for the perforated opening 116 to stretch and widen, due to the thickness of the gloves and friction between the gloves and edges of the opening, rendering the plastic layer 114 even less effective in singularizing the gloves 107.

As a result, because the disposable glove industry is very cost sensitive, most manufacturers of glove dispensing boxes omit the clear plastic layer 114 altogether. And even if a more sophisticated box 100 were provided that was able to singularize the gloves, it would likely fail commercially, because it would be produced in lower quantities as a "specialty" item, and would therefore cost significantly more than existing glove dispensing box designs.

What is needed, therefore, is an apparatus and method for singularizing disposable gloves dispensed from a glove dispensing box without significantly increasing the manufacturing cost of the glove dispensing box.

SUMMARY OF THE INVENTION

The present invention is an apparatus that is independent of and applicable to a glove dispensing box, and a method for singularizing gloves dispensed from a glove dispensing box, that do not increase the manufacturing cost of the glove dispensing box.

The disclosed invention is an accessory that can be attached to an existing glove dispensing box to singularize the glove dispensing therefrom. Since the disclosed apparatus is a separate accessory that is easily adapted to a wide variety of glove dispensing box designs, there is no impact whatsoever on the manufacturing cost of the glove dispensing boxes themselves. In particular, there is no need to make any costly design or manufacturing changes to the dispensing boxes as they are currently manufactured. The high cost of implementing a new, dedicated, specialty product line of dispensing boxes is thereby avoided, because the same glove dispensing boxes can be used both for applications where singularizing of the gloves is not required, and for applications where singularizing of the gloves is required, with the only difference being that the disclosed accessory is employed only in the latter case.

According to the present disclosure, a "frangible" cover is provided that is attachable to a glove dispensing box such that it covers the dispensing region thereof. The cover is referred to herein as "frangible" because it includes at least one longitudinal slit or longitudinal perforation that can be "opened," either by breaking through longitudinal perforations or spreading apart the edges of a longitudinal slit. The frangible cover is sufficiently thick and stiff to ensure that, as a glove is removed from the glove dispensing box, the separated sides of the opened longitudinal slit or longitudinal perforation will apply a frictional resistance that is sufficient to overcome any mutual adherence of the gloves to each other, so that any additional gloves that may have adhered themselves to the selected glove are scraped away and blocked from being drawn out of the dispensing box.

In embodiments, the frangible cover is a transparent or translucent polymeric cover. In various embodiments, the polymeric material of the cover is selected for its flexibility and durability, ensuring that it can withstand repeated use without stretching, tearing, or otherwise losing effectiveness. For example, in some embodiments the frangible cover is made from a polyester film (polyethylene terephthalate, PET), such as Mylar™, having a thickness of at least 0.003 inches, preferably between 0.003 inches and 0.007 inches, and in exemplary embodiments substantially equal to 0.005 inches. In other embodiments, the frangible cover is made from a biodegradable polymer, such as a cellulose-based polymer.

In embodiments, the frangible cover is directly fixable to the dispensing box, for example by an adhesive or by attachment bands. In still other embodiments, the frangible cover is a sleeve, such as a silicon sleeve, into which the dispensing box can be inserted, and positioned such that the longitudinal slit or longitudinal perforation is positioned above the dispensing region of the box. Attachment of the frangible cover by an adhesive, for example by peeling away a protective sheet to expose an underlying pressure-activated adhesive, can be preferred for applications where convenience is most important, while attachment by bands or by a sleeve may be preferable when it is most important to minimize costs by re-using the same apparatus for a plurality of glove dispensing boxes as they are consumed.

A first general aspect of the present invention is an accessory that is attachable to a glove dispensing box. The accessory is configured to singularize gloves as they are removed from the glove dispensing box. The accessory includes a frangible cover configured for attachment thereof to a glove dispensing box containing a plurality of gloves, and a longitudinal slit or longitudinal perforation provided in the frangible cover, the longitudinal slit or longitudinal perforation being located over a dispensing region of the glove dispensing box when the frangible cover is attached to the glove dispensing box.

The accessory is configured such that when the longitudinal slit or longitudinal perforation is opened, a selected one of the plurality of gloves can be grasped and removed from the glove dispensing box through the dispensing region and the longitudinal slit or longitudinal perforation, while separated sides of the opened longitudinal slit or longitudinal perforation apply a frictional resistance that overcomes any mutual adherence between the plurality of gloves, so that any additional gloves of the plurality of gloves that may have become mutually adhered to the selected one of the plurality of gloves are scraped away and blocked from being drawn out of the dispensing box.

In embodiments, the frangible cover is a polymeric cover.

In any of the above embodiments, the frangible cover can be attachable to the glove dispensing box by an adhesive. In some of these embodiments, the adhesive is a layer of cover adhesive applied to a downward-facing side of the frangible cover, the layer of cover adhesive being suitable for attachment of the frangible cover to the glove dispensing box such that the longitudinal slit or longitudinal perforation is positioned above the dispensing region of the glove dispensing box. Some of these embodiments further include a protective sheet removably applied to the layer of cover adhesive, wherein removal of the protective sheet from the layer of cover adhesive exposes the layer of cover adhesive so that it can be adhered to the glove dispensing box. In some of these embodiments, the protective sheet comprises a grasping region that extends beyond the cover adhesive and is configured to facilitate grasping of the protective sheet and pulling of the protective sheet away from the frangible cover, or at least one cut through the protective sheet that enables an edge of the at least one cut to be grasped, thereby facilitating removal of the protective sheet away from the frangible cover.

In any of the above embodiments, at least one end of the longitudinal slit or longitudinal perforation can terminate in a terminating hole that penetrates the frangible cover.

In any of the above embodiments, the dispensing region and the frangible cover can be elongated and approximately rectangular.

Or the dispensing region can be round or square, in which case the frangible cover comprises a plurality of longitudinal slits or longitudinal perforations extending radially outward from a center of the frangible cover. In some of these embodiments, the longitudinal slits or longitudinal perforations extend radially outward from a central hole penetrating the frangible cover, and each of the longitudinal slits or longitudinal perforations terminates in a terminating hole that penetrates the frangible cover.

In any of the above embodiments, the frangible cover can be removably attachable to the glove dispensing box by at least one elastic band configured to surround the glove dispensing box.

In any of the above embodiments, the frangible cover can be a sleeve into which the glove dispensing box can be inserted such that the longitudinal slit or longitudinal perforation is located above the dispensing region of the glove dispensing box.

In any of the above embodiments, a thickness of the frangible cover can be equal to or greater than 0.003 inches.

In any of the above embodiments, the frangible cover can be made from a polyester (polyethylene terephthalate, PET) film.

Any of the above embodiments can further include at least one transverse perforation or slit that intersects the longitudinal slit or perforation.

A second general aspect of the present invention is a method of singularizing gloves as they are removed from a glove dispensing box. The method includes providing a glove dispensing box containing a plurality of gloves therein and comprising a dispensing region thereof through which the gloves can be dispensed, providing a glove singularizing accessory, the glove singularizing accessory comprising a frangible cover configured for attachment thereof to the glove dispensing box, the frangible cover comprising a longitudinal slit or longitudinal perforation thereof, attaching the frangible cover to the glove dispensing box, the longitudinal slit or longitudinal perforation being thereby located over the dispensing region of the glove dispensing box, opening the longitudinal slit or longitudinal perforation, reaching through the opened longitudinal slit or longitudinal perforation and dispensing region, and grasping a selected one of the gloves within the glove dispensing box, and withdrawing the selected one of the gloves through the dispensing region and the opened longitudinal slit or longitudinal perforation, while separated sides of the opened longitudinal slit or longitudinal perforation apply a frictional resistance that overcomes any mutual adherence between the plurality of gloves, so that any additional gloves of the plurality of gloves that may have become mutually adhered to the selected one of the plurality of gloves are scraped away and blocked from being withdrawn from the dispensing box.

In embodiments, the frangible cover is a polymeric cover.

In any of the above embodiments, attaching the frangible cover to the glove dispensing box can include causing an adhesive to adhere the frangible cover to the glove dispensing box.

In any of the above embodiments, at least one elastic band can extend between opposing edges of the frangible cover, and attaching the frangible cover to the glove dispensing box can include causing the at least one elastic band to surround the glove dispensing box.

In any of the above embodiments, the frangible cover can be a sleeve, and attaching the frangible cover to the glove dispensing box can include inserting the glove dispensing box into the sleeve and positioning the glove dispensing box such that the longitudinal slit or longitudinal perforation is located above the dispensing region of the glove dispensing box.

In any of the above embodiments, the glove singularizing accessory can further include a layer of cover adhesive applied about a periphery of a downward facing side of the frangible cover, a protective sheet can be removably applied to the layer of cover adhesive, and attaching the frangible cover to the glove dispensing box can include removing the protective sheet from the layer of cover adhesive, thereby exposing the layer of cover adhesive so that it can be caused to adhere the frangible cover to the glove dispensing box.

The features and advantages described herein are not all-inclusive and, in particular, many additional features and advantages will be apparent to one of ordinary skill in the art in view of the drawings, specification, and claims. Moreover, it should be noted that the language used in the specification has been principally selected for readability and instructional purposes, and not to limit the scope of the inventive subject matter.

BRIEF DESCRIPTION OF THE DRAWINGS

FIG. 1C is a perspective view of the disposable glove dispensing box of FIG. 1A shown with a plurality of gloves being simultaneously dispensed therefrom;

FIG. 4B is a perspective view of the embodiment of FIG. 2 applied to the glove dispensing box of FIG. 4A, showing a singularized glove being withdrawn from the glove dispensing box through the applied embodiment of FIG. 2;

FIG. 7 is a perspective view of a singularized glove being withdrawn from the glove dispensing box of FIG. 5A through the applied embodiment of FIG. 5B;

FIG. 8 is a perspective view of an embodiment that is similar to FIG. 4B, but in which the frangible cover is attached to the glove dispensing box by a pair of elastic straps; and FIG. 9 is a perspective view of an embodiment in which the frangible cover is a sleeve into which the glove dispensing box can be inserted.

DETAILED DESCRIPTION

The present invention is an apparatus that is independent of and applicable to a glove dispensing box, and a and method for singularizing gloves dispensed from a glove dispensing box, that do not increase the manufacturing cost of the glove dispensing box.

More specifically, the disclosed invention is a singularizing accessory that can be attached to an existing glove dispensing box so as to singularize the glove dispensing therefrom. Since the disclosed apparatus is a separate accessory that is easily adapted to a wide variety of box designs, there is no impact on the manufacturing cost of the glove dispensing boxes themselves. In particular, there is no need for any costly re-design or manufacturing changes to glove dispensing boxes as they are currently produced. The high cost of implementing a new, dedicated specialty product line of glove dispensing boxes is thereby avoided.

Figure 2:
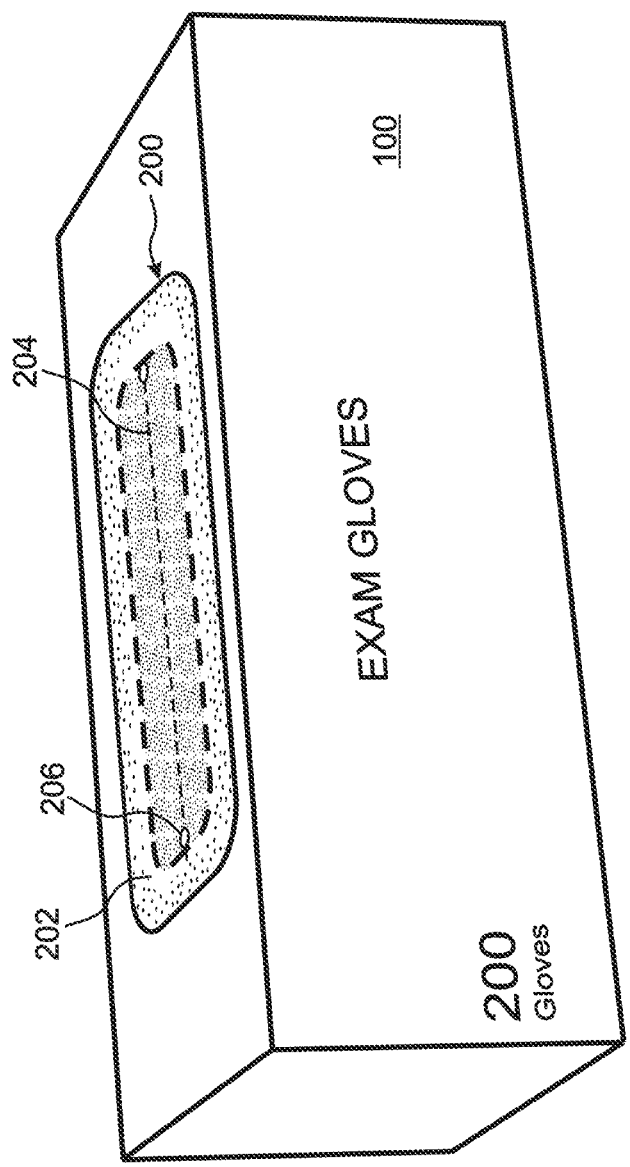
FIG. 2 is a perspective view of a substantially rectangular embodiment of the present invention applied to the glove dispensing box of FIG. 1A.

With reference to FIG. 2, the disclosed singularizing accessory includes a flat, frangible cover 200 that is attachable to a glove dispensing box 100 such that a longitudinal perforation 204 provided in the frangible cover 200 is located over the dispensing region 102 of the box 100. In similar embodiments, as is discussed in more detail with reference to FIG. 3B, a longitudinal slit 205 is provided instead of a longitudinal perforation 204. It will be understood that the illustrations of longitudinal perforations 204, 604, 904 that are included in the present drawings are intended to represent either longitudinal slits or longitudinal perforations, unless otherwise explicitly stated herein.

The frangible cover 200 is sufficiently thick and stiff to ensure that, as a selected glove 400 is removed from the glove dispensing box 100, the separated sides of the opened longitudinal slit 205 or longitudinal perforation 204 will apply a frictional resistance that is sufficient to overcome any mutual adherence of the gloves to each other, so that any additional gloves that may have become adhered to the selected glove 400 are scraped away and blocked from being drawn out of the dispensing box 100.

In embodiments, the frangible cover 200 is a transparent or translucent polymeric cover. In various embodiments, the frangible cover 200 is made from a polymeric material selected for its flexibility and durability, ensuring it can withstand repeated use without stretching, tearing, or otherwise losing effectiveness. For example, in some embodiments the frangible cover 200 is made from a polyester (polyethylene terephthalate, PET) film, such as Mylar™, having a thickness that is at least 0.003 inches, preferably between 0.003 inches and 0.007 inches, and in exemplary embodiments substantially equal to 0.005 inches. In other embodiments, the frangible cover 200 is made from a biodegradable polymer, such as a cellulose-based polymer.

Figure 3A:
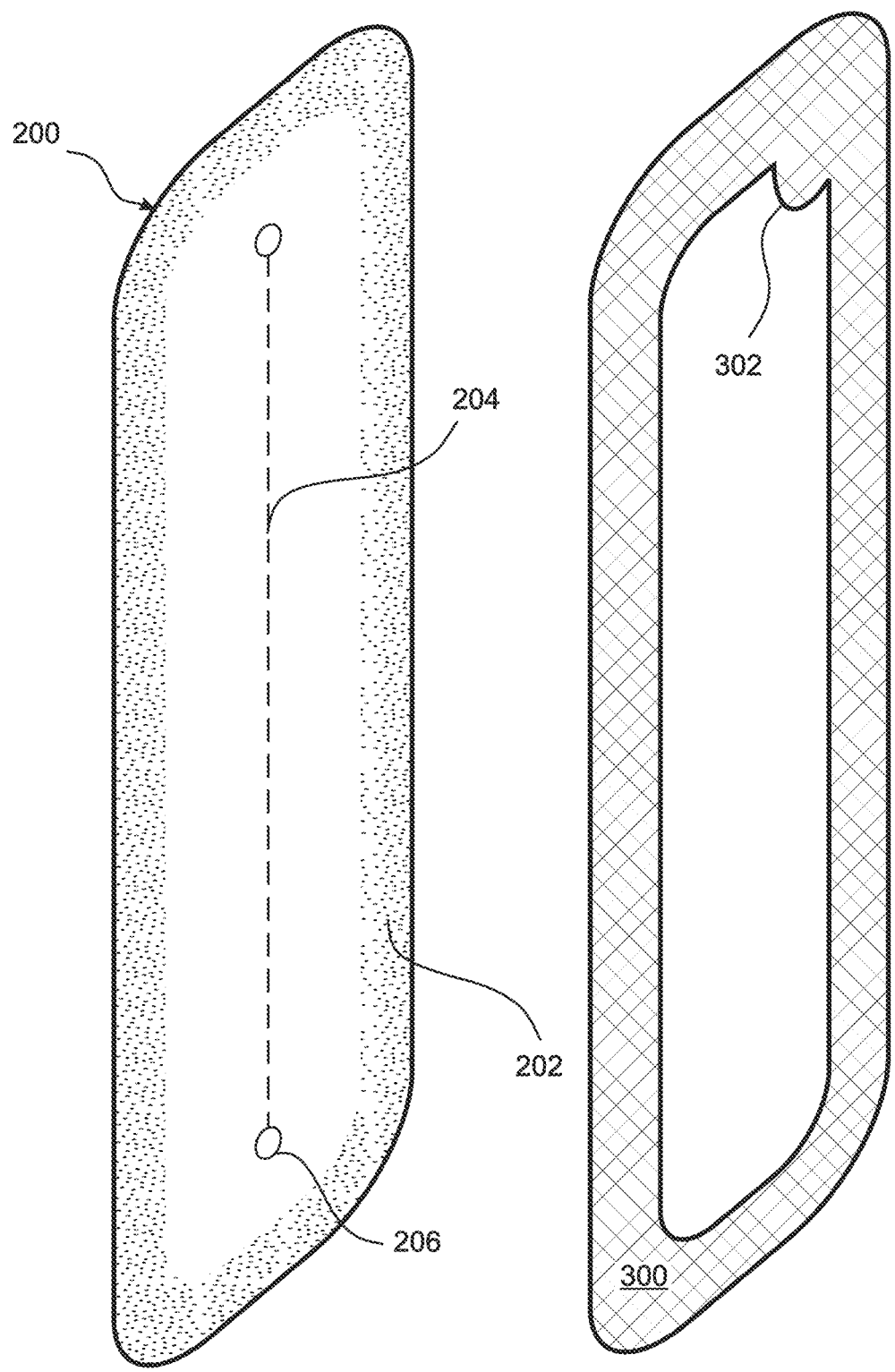
FIG. 3A is a perspective exploded view of the embodiment of FIG. 2 showing the separated frangible cover with applied adhesive and protective sheet configured to cover the applied adhesive.
Figure 3B:
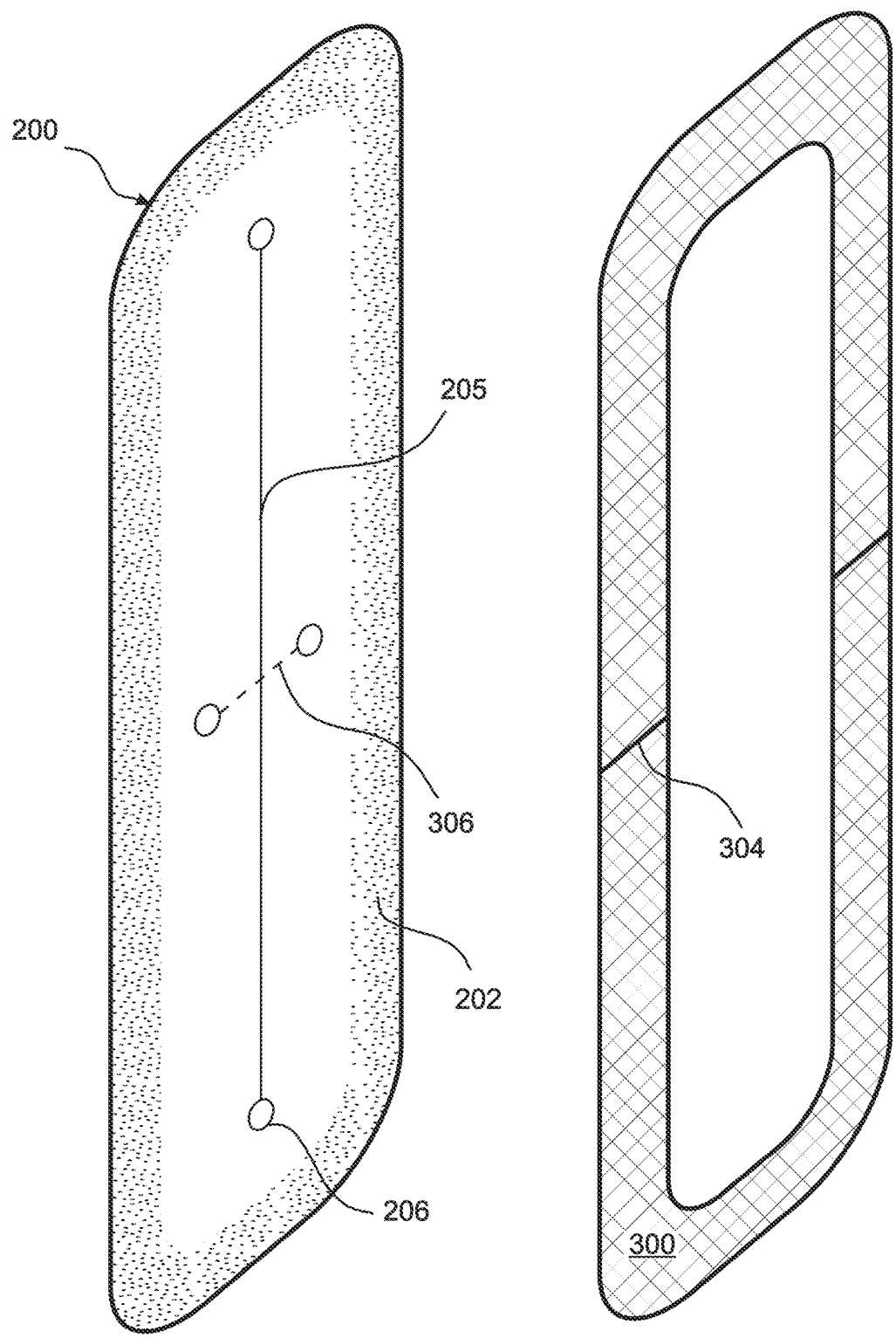
FIG. 3B is a perspective exploded view of an embodiment that is similar to FIG. 3A, except that the frangible cover includes a longitudinal slit rather than a longitudinal perforation, and further includes a transverse perforation.

FIG. 3A is and exploded view of the embodiment 200 of FIG. 2 in which the frangible cover 200 comprises a longitudinal perforation 204, whereas in FIG. 3B a similar embodiment includes a longitudinal slit 205 instead of a longitudinal perforation 204. In the illustrated embodiments, a layer of a pressure-activated cover adhesive 202 is applied proximate the periphery of a downward-facing side of the frangible cover 200, with the cover adhesive 202 being initially covered by a protective sheet 300 that can be peeled away to expose the cover adhesive 202 for attachment to the dispensing box 100. The protective sheet 300 of FIG. 3A includes a grasping region 302 that extends inward beyond the cover adhesive 202 and can be readily grasped by a user to facilitate grasping of the protective sheet 300 and pulling of the protective sheet 300 away from the frangible cover 200. In similar embodiments the grasping region 302 extends outward beyond the periphery of the frangible cover 200.

Instead of a grasping region 302, removal of the protective sheet 300 is facilitated in the embodiment of FIG. 3B by including cuts 304 that divide the protective sheet 300 into two halves. By slightly flexing the frangible cover 200, the edges of the cuts 304 can be easily grasped, enabling the protective sheet 300 to be removed.

It can further be seen that the embodiment of FIG. 3B includes a transverse perforation 306 that is orthogonal to the longitudinal slit 205. In various embodiments, at least one orthogonal perforation 306 or orthogonal slit (not shown) is included, which functions to facilitate insertion by a user's hand more deeply into the glove dispensing box 100 through the location where the longitudinal and orthogonal slit(s) or perforation(s) intersect, while the remaining portions of the longitudinal perforation 204 or slit 205 are largely unaffected and continue to singularize the gloves.

In the embodiment of FIG. 3B, the initial insertion of the user's hand through the longitudinal slit 205 into the upper region of the glove dispensing box 100 does not apply sufficient force to open the transverse perforation 306. However, when it becomes necessary for the user to insert a larger portion of a hand through the longitudinal slit 205, for example to reach gloves near the bottom of the glove dispensing box 100, the transverse perforation 306 is opened, thereby reducing the resistance to penetration by the user's hand. Similar embodiments provide a similar effect by combining a longitudinal perforation 204 with at least one orthogonal perforation 306, and by adjusting the sizes and spacing of the perforations such that opening the longitudinal perforation 204 requires less force than opening the orthogonal perforation 306. In some embodiments, glove singularization is enhanced by increasing a roughness of the edges of the longitudinal slit 205, or by adjusting a configuration of the spacings and/or depths of the perforations of a longitudinal perforation 204.

In various embodiments, the frangible cover 200 comprises a plurality of mutually orthogonal slits or perforations that converge at a common location along the longitudinal perforation 204 or slit 205. For example, in some embodiments the frangible cover 200 comprises three orthogonal slits or perforations that intersect with the longitudinal perforation 204 or slit 205 at angles of 45 degrees, 90 degrees, and 130 degrees, respectively.

It can also be seen in FIGS. 3A and 3B that the longitudinal slit 205 or longitudinal perforation 204 and the transverse perforation are terminated at each end by small holes 206 provided in the frangible cover 200. These holes significantly reduce any possibility that the frangible cover 200 might tear when the longitudinal slit 205 or longitudinal perforation 204 is opened, thereby inadvertently lengthening the resulting opening.

Figure 1A:
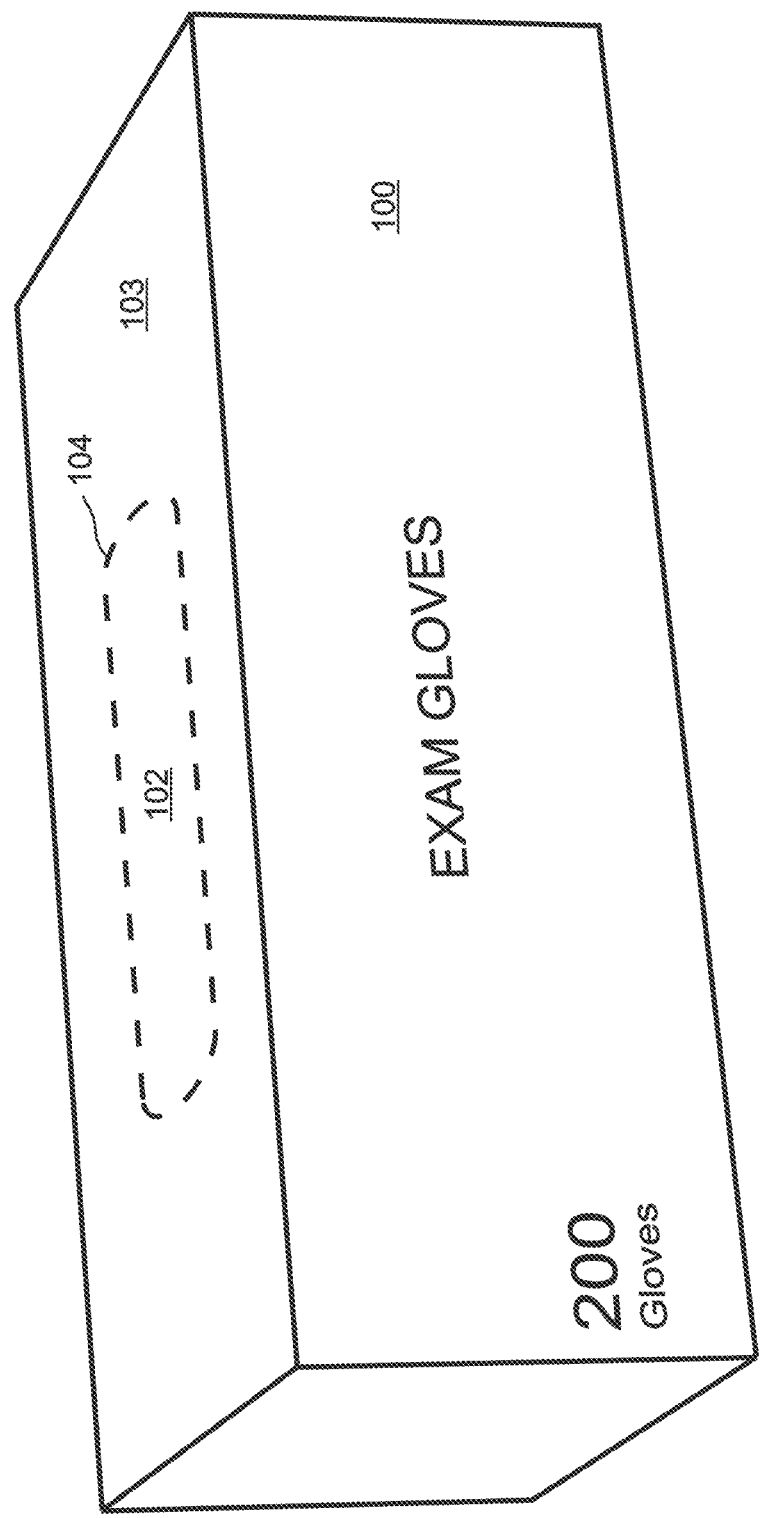
FIG. 1A is a perspective view of an unopened disposable glove dispensing box of the prior art.
Figure 1B:
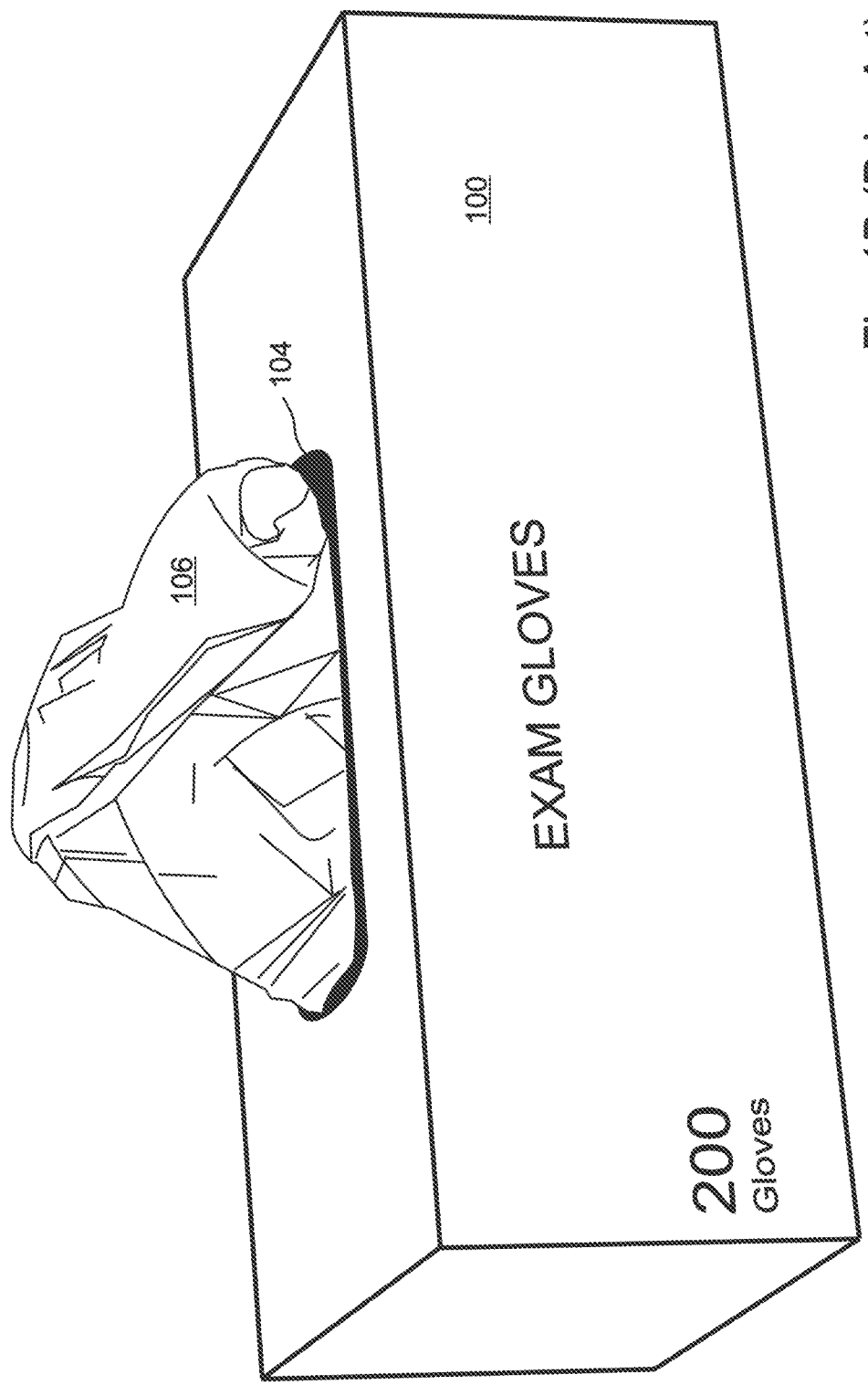
FIG. 1B is a perspective view of the disposable glove dispensing box of FIG. 1A shown after it has been opened and a plurality of gloves have been partially dispensed therefrom.
Figure 1D:
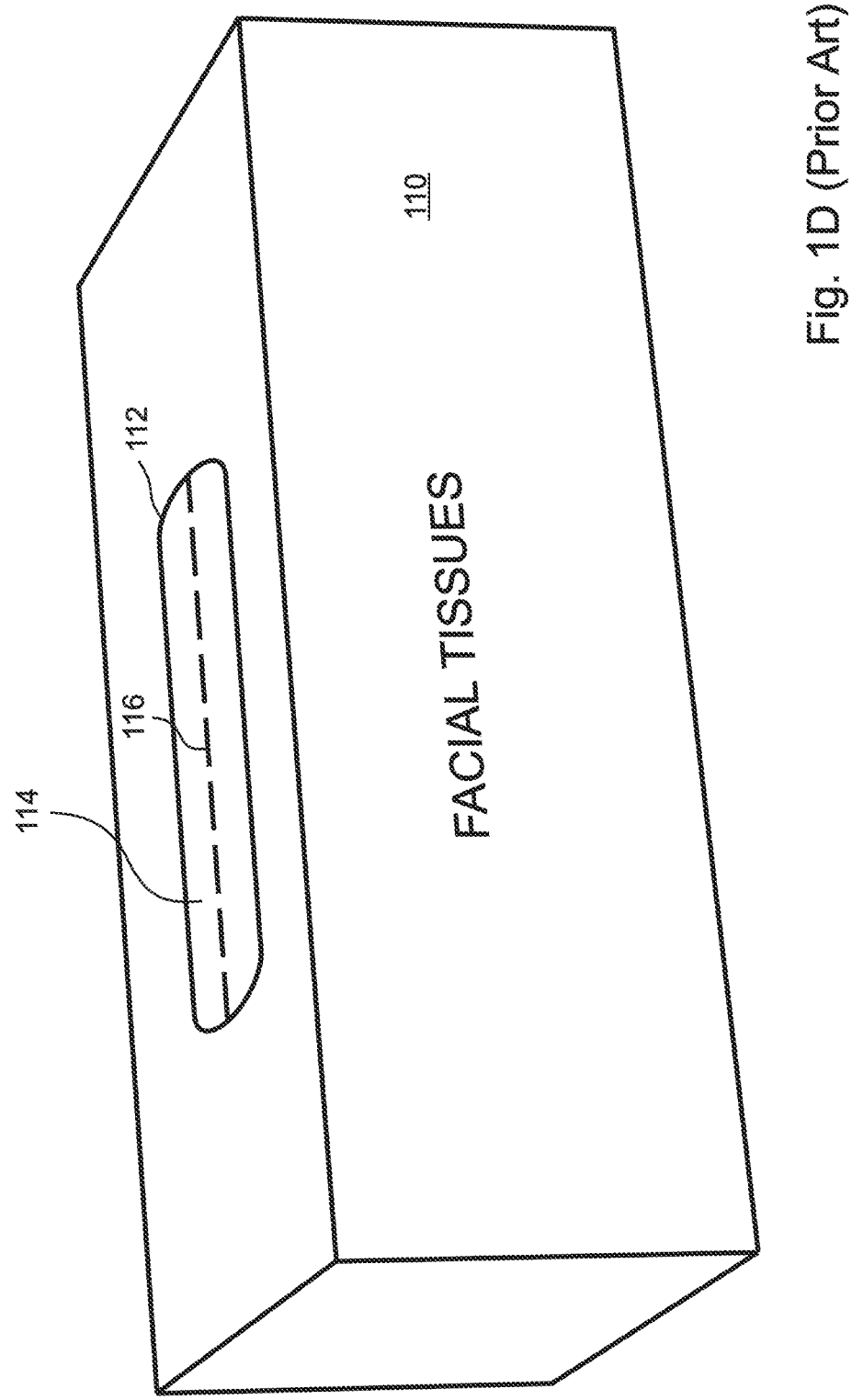
FIG. 1D is a perspective view of an unopened tissue dispensing box of the prior art.
Figure 1E:
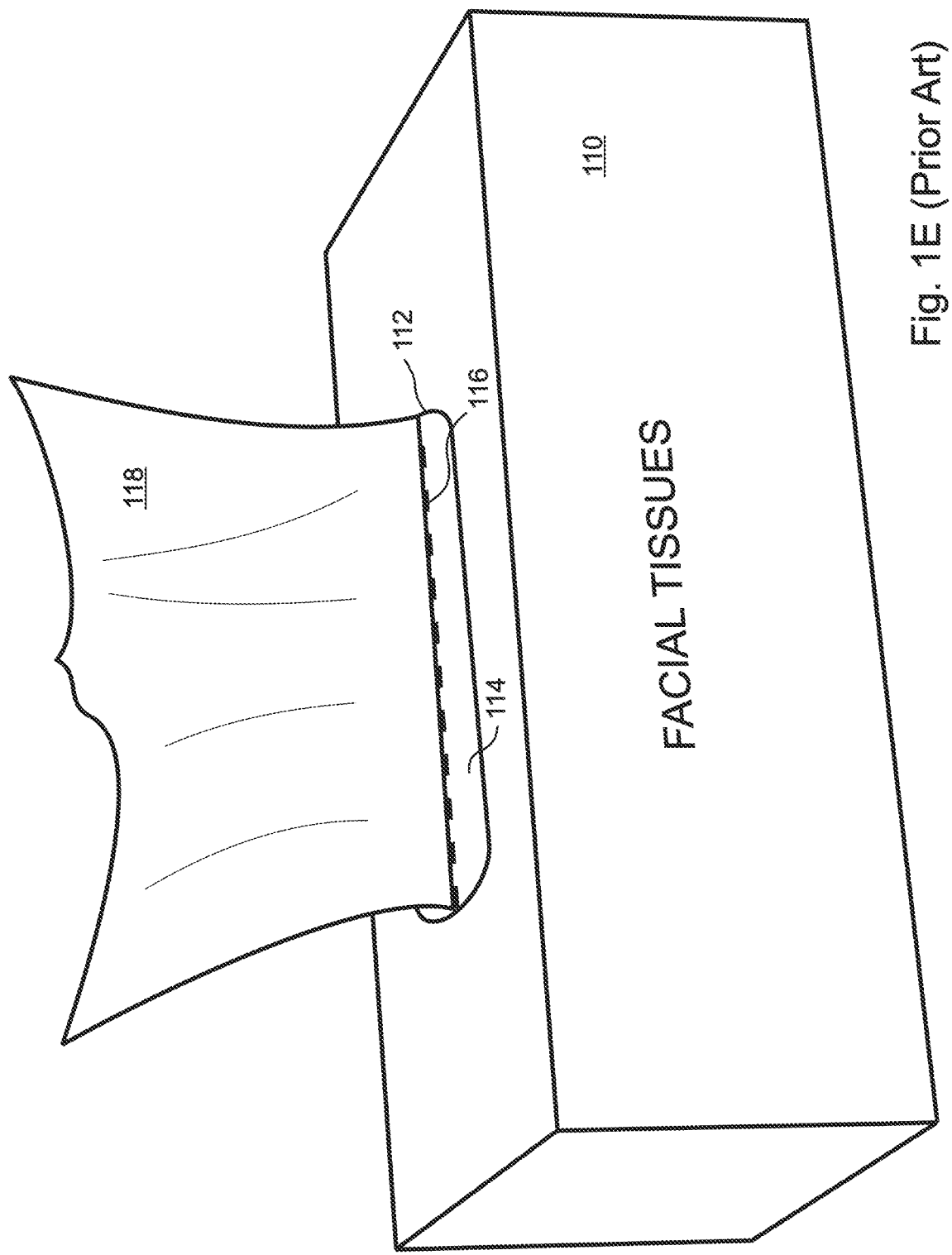
FIG. 1E is a perspective view of the tissue dispensing box of FIG. 1D, shown with a single tissue having been partially dispensed therefrom.
Figure 4A:
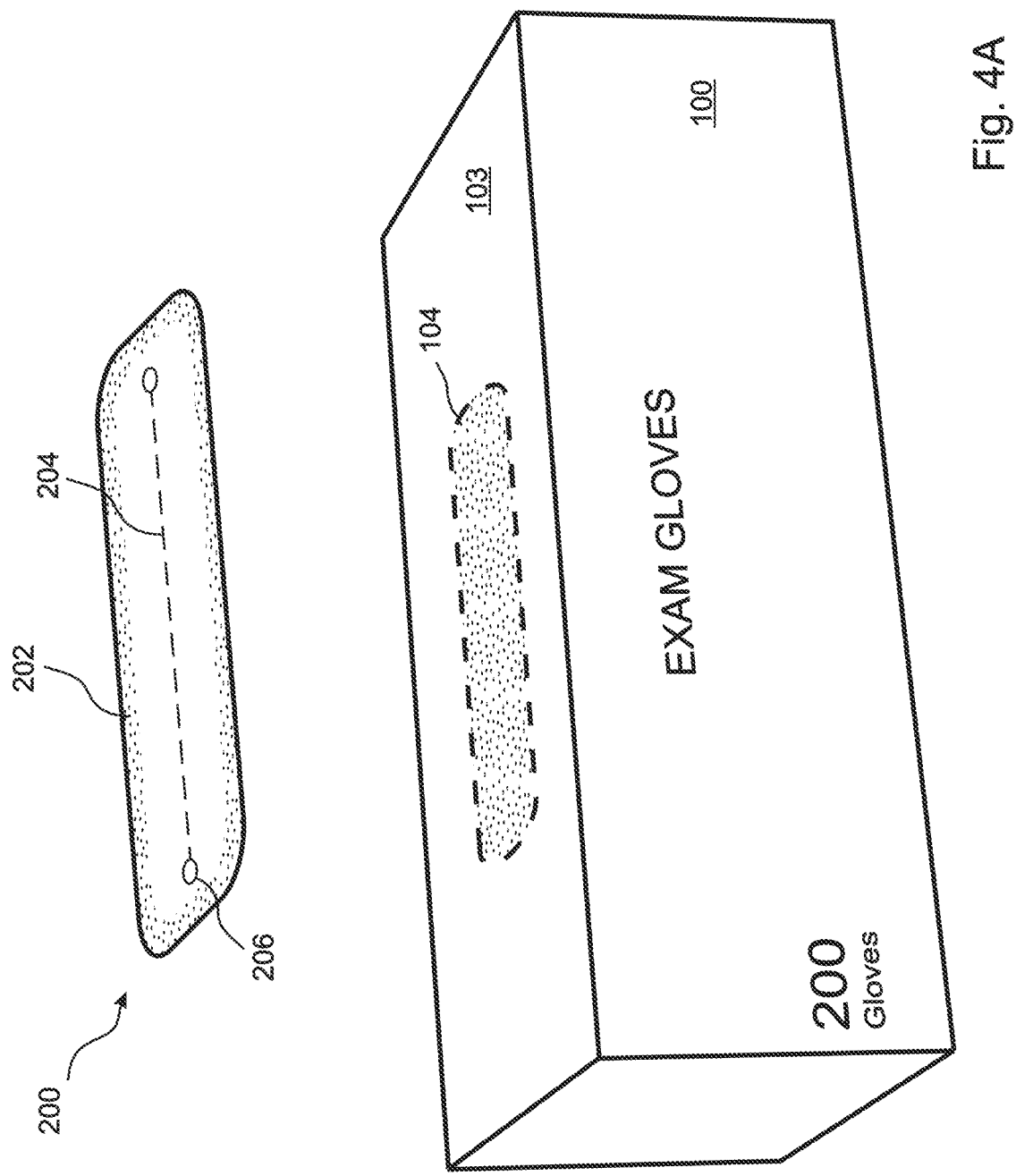
FIG. 4A is a perspective view of the embodiment of FIG. 2 positioned above the glove dispensing box of FIG. 1A after removal therefrom of the protective sheet.

FIG. 4A illustrates the embodiment of FIG. 2 positioned above the dispensing region 102 of the glove dispensing box 100 of FIG. 1A. In the figure, the cover panel has been removed from the dispensing region 102 by breaking the frangible longitudinal slit or longitudinal perforation 104 that surrounds the dispensing region 102, and the protective sheet 300 has been removed from the frangible cover 200, thereby exposing the cover adhesive 202. FIG. 4B illustrates the assembled dispensing box 100 and singularizing accessory 200. In FIG. 4B, the longitudinal slit 205 or longitudinal perforation 204 of the frangible cover 202 has been opened, and a single glove 400 has been partially removed through the resulting opening. Any additional gloves that might have become attached to the removed glove have been scraped away by the stiff sides of the opened longitudinal slit 205 or longitudinal perforation 204, such that only the selected glove 400 is removed from the glove dispensing box 100.

Figure 5:
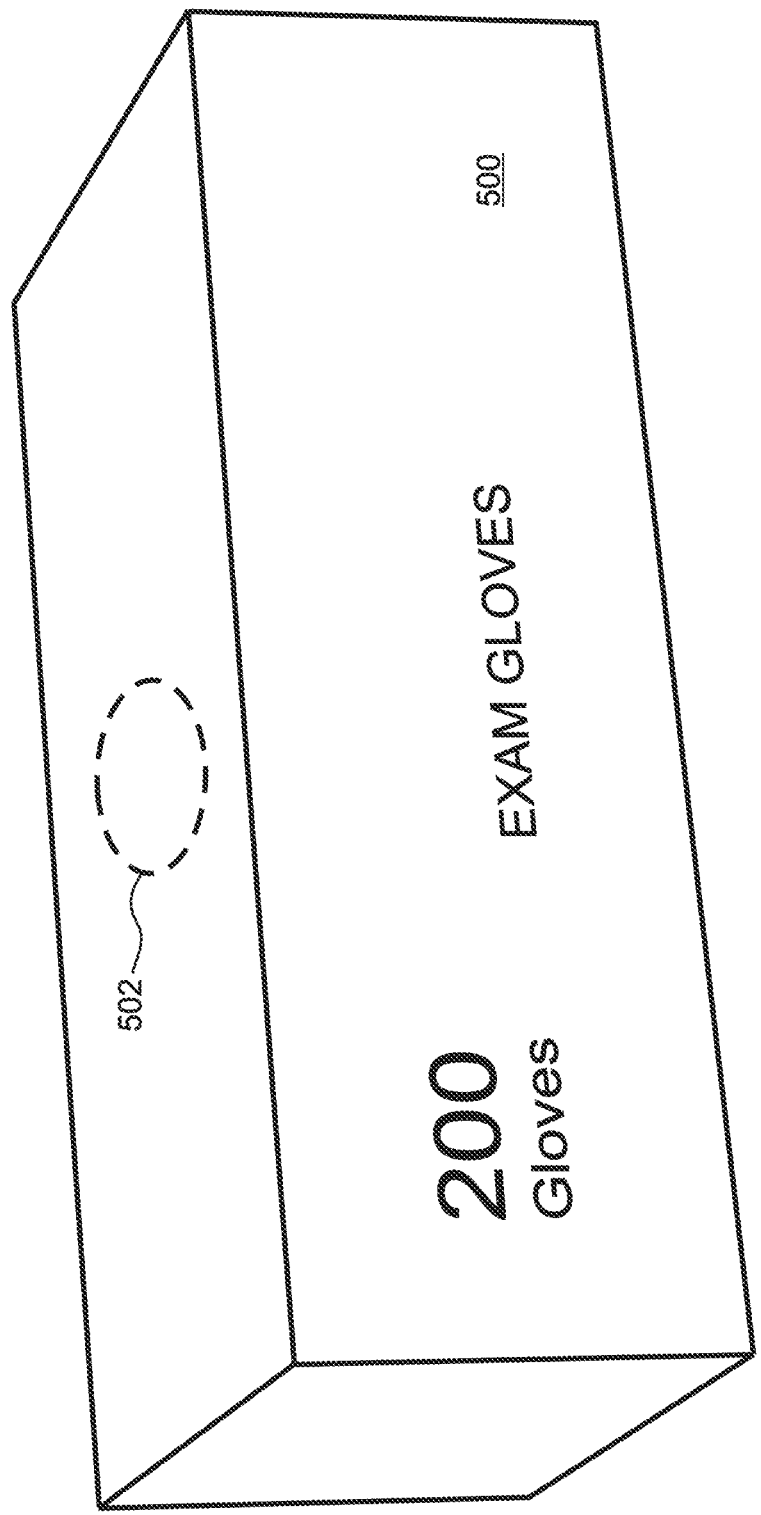
FIG. 5 is a perspective view of a glove dispensing box of the prior art that includes a round dispensing region.
Figure 6A:
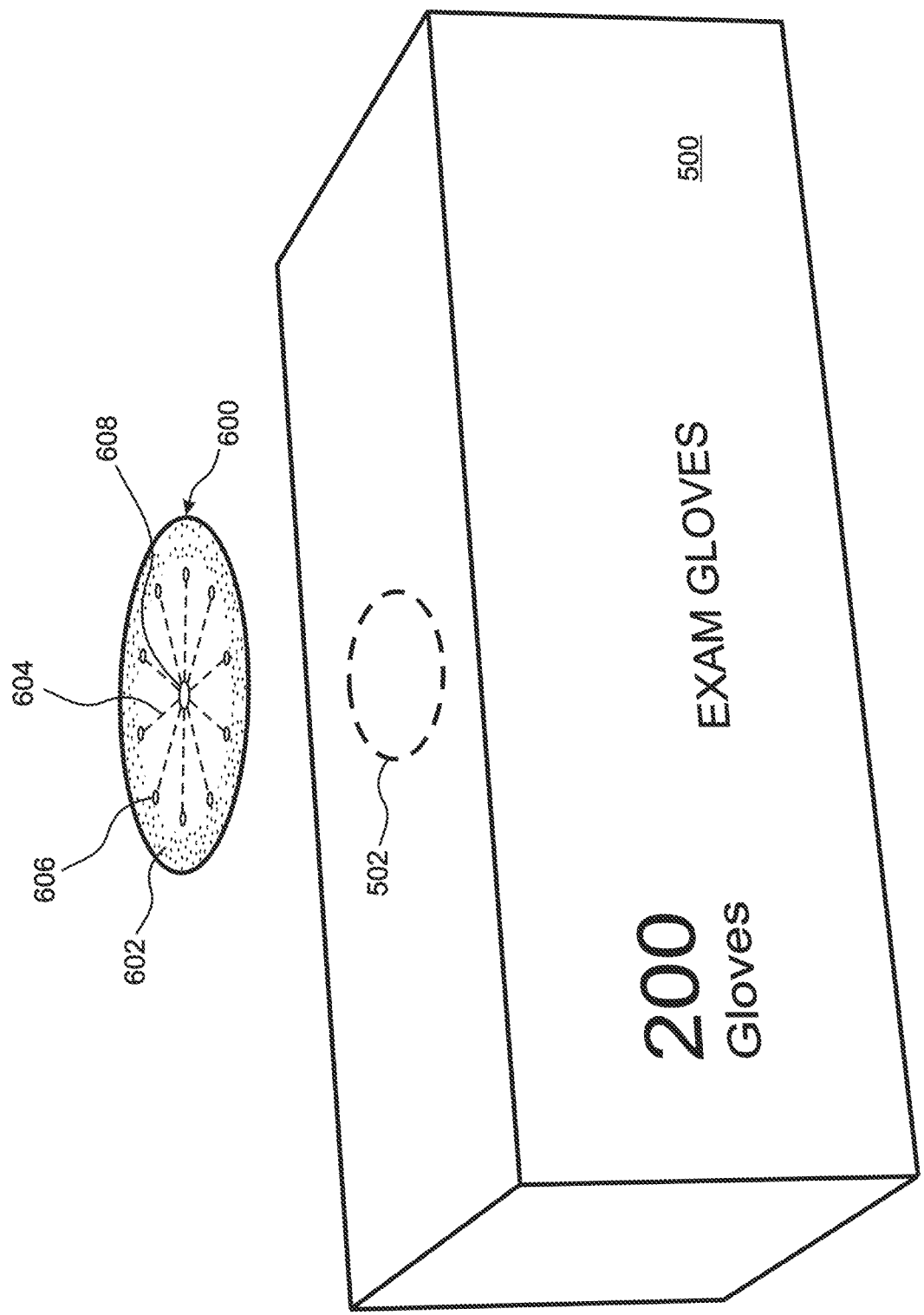
FIG. 6A is a perspective view of a substantially round embodiment of present invention positioned above the glove dispensing box of FIG. 5.

FIG. 5 is a perspective view of a glove dispensing box 500 of the prior art that is similar to the glove dispensing box 100 of FIG. 1A, except that the dispensing region 502 is a round opening centered on the upper surface of the glove dispensing box 500. FIG. 6A illustrates an embodiment 600 of the disclosed singularizing accessory positioned above the glove dispensing box 500 of FIG. 5. In this embodiment, the frangible cover 600 is round and, attachable to the glove dispensing box 500 by an adhesive 602. The frangible cover 600 comprises a plurality of linear frangible longitudinal slit or longitudinal perforations 604 extending radially inward to an open hole 608 at the center of the frangible cover. The radially outward ends of the longitudinal slits or longitudinal perforations 604 terminate in small holes 606 that function in a similar manner to the small holes 206 of FIGS. 2 through 4B.

Figure 6B:
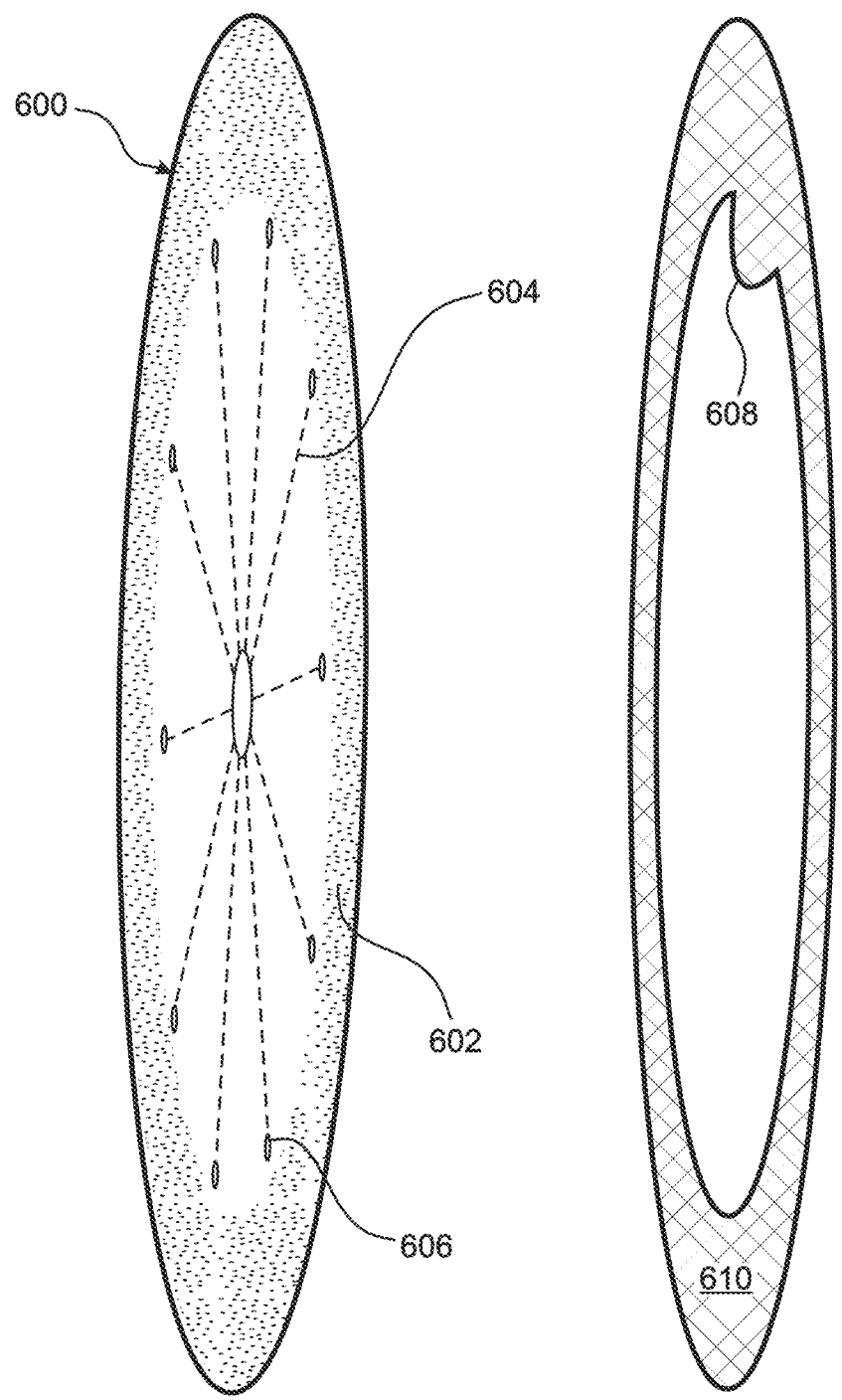
FIG. 6B is an exploded view of the embodiments of FIG. 6A, showing a separated frangible cover with applied adhesive and protective sheet that is configured to cover the applied adhesive

FIG. 6B is an exploded view of the embodiment 600 of FIG. 6A, which includes a protective sheet 610 and a grasping region 608 thereof that function in a manner similar to the protective sheet 300 and grasping region 302 of FIG. 3.

FIG. 7 is a perspective view that illustrates the glove dispensing box 500 of FIG. 5 to which the frangible cover 600 of FIGS. 6A and 6B has been applied. In FIG. 7, the longitudinal slit or longitudinal perforations 604 of the frangible cover 600 have been broken, and a glove 400 has been partially removed from the glove dispensing box 500.

FIGS. 2-7 illustrate embodiments in which the singularizing accessory 200, 600 is attached to the glove dispensing box 100 by an adhesive 302. With reference to FIG. 8, in other embodiments the singularizing accessory 800 is removably attached to the glove dispensing box 100. In the embodiment of FIG. 8, a singularizing accessory 800 that is similar to the accessory 200 of FIG. 2 is attached to the box 100 by a pair of elastic bands 802, rather than by an adhesive.

With reference to FIG. 9, in similar embodiments the frangible cover 900 is a monolithic sleeve, such as a silicone sleeve, into which the dispensing box 100 can be inserted and positioned such that the frangible longitudinal slit 904 or longitudinal perforation is above the dispensing region 202 of the box 100. In the illustrated embodiment, the longitudinal slit 904 terminates at small holes 906 that help to prevent tearing and lengthening of the slit 904 during use.

Embodiment in which the singularizing accessory 800, 900 is removably attached to the glove dispensing box 100 offer the dual advantage of enabling the accessory 800, 900 to be removed and replaced if it becomes worn or otherwise ineffective, while also enabling the same accessory 800, 900, while it is still effective, to be used successively on several glove dispensing boxes 100 as they are depleted and replaced.

While the embodiments that are illustrated herein are applied to rectangular 100 glove dispensing boxes having rectangular or round dispensing regions 104, 502, it will be understood by those of skill in the art that the inventive concepts described herein are equally applicable to glove dispensing boxes and dispensing regions thereof having other shapes, such as square, hexagonal, etc.

The foregoing description of the embodiments of the invention has been presented for the purposes of illustration and description. Each and every page of this submission, and all contents thereon, however characterized, identified, or numbered, is considered a substantive part of this application for all purposes, irrespective of form or placement within the application. This specification is not intended to be exhaustive or to limit the invention to the precise form disclosed. Many modifications and variations are possible in light of this disclosure.

Although the present application is shown in a limited number of forms, the scope of the disclosure is not limited to just these forms, but is amenable to various changes and modifications. The present application does not explicitly recite all possible combinations of features that fall within the scope of the disclosure. The features disclosed herein for the various embodiments can generally be interchanged and combined into any combinations that are not self-contradictory without departing from the scope of the disclosure. In particular, the limitations presented in the dependent claims below can be combined with their corresponding independent claims in any number and in any order without departing from the scope of this disclosure, unless the dependent claims are logically incompatible with each other.

What is claimed is:

1. An accessory that is attachable to a glove dispensing box, the accessory comprising:
    a glove dispensing box containing and fully enclosing a plurality of gloves, the glove dispensing box being packaged for sale to a user in glove dispensing box packaging;
    an elongated and approximately rectangular frangible cover distinct and fully separated from said glove dispensing box, the frangible cover being packaged for sale to the user in frangible cover packaging that is distinct from the glove dispensing box packaging, the frangible cover being configured for direct attachment and fixing thereof by the user to the glove dispensing box;
    a linear longitudinal perforated slit provided in the frangible cover; and
    a linear transverse perforated slit provided in the frangible cover, wherein:
        the transverse perforated slit is perpendicular to the longitudinal perforated slit;
        an intersection between the longitudinal perforated slit and the transverse perforated slit is located substantially at centers of both the longitudinal perforated slit and the transverse perforated slit;
        a length of the longitudinal perforated slit is at least twice as long as a length of the transverse perforated slit;
        both ends of the longitudinal perforated slit and both ends of the transverse perforated slit terminate in terminating holes that penetrate the frangible cover; and
        the longitudinal perforated slit and the transverse perforated slit are the only openings that are provided in the frangible cover;
    wherein the accessory is configured such that when the glove dispensing box and frangible cover are removed from their respective packaging, and when the frangible cover is attached to the glove dispensing box, the longitudinal perforated slit and the transverse perforated slit being located over a dispensing region of the glove dispensing box, and when the longitudinal perforated slit and the transverse perforated slit are opened and a user's hand is inserted therethrough, a selected one of the plurality of gloves can be grasped by the user's hand and removed from the glove dispensing box through the dispensing region and through the longitudinal perforated slit and the transverse perforated slit, while separated sides of the opened longitudinal perforated slit and the transverse perforated slit apply a frictional resistance that overcomes any mutual adherence between the plurality of gloves, so that any additional gloves of the plurality of gloves that may have become mutually adhered to the selected one of the plurality of gloves are scraped away and blocked from being drawn out of the glove dispensing box.

2. The accessory of claim 1, wherein the frangible cover is a polymeric cover.

3. The accessory of claim 1, wherein the frangible cover is attachable to the glove dispensing box by an adhesive.

4. The accessory of claim 3, wherein the adhesive is a layer of cover adhesive applied to a downward-facing side of the frangible cover, the layer of cover adhesive being suitable for attachment of the frangible cover to the glove dispensing box such that the longitudinal perforated slit is positioned above the dispensing region of the glove dispensing box.

5. The accessory of claim 4, further comprising a protective sheet removably applied to the layer of cover adhesive, wherein removal of the protective sheet from the layer of cover adhesive exposes the layer of cover adhesive so that it can be adhered to the glove dispensing box.

6. The accessory of claim 5, wherein the protective sheet comprises at least one of:
    a grasping region that extends beyond the cover adhesive and is configured to facilitate grasping of the protective sheet and pulling of the protective sheet away from the frangible cover; and at least one cut through the protective sheet that enables an edge of the at least one cut to be grasped, thereby facilitating removal of the protective sheet away from the frangible cover.

7. The accessory of claim 1, wherein the frangible cover is removably attachable to the glove dispensing box by at least one elastic band configured to surround the glove dispensing box.

8. The accessory of claim 1, wherein a thickness of the frangible cover is equal to or greater than 0.003 inches.

9. The accessory of claim 1, wherein the frangible cover is made from a polymeric material.

10. A method of singularizing gloves as they are removed from a glove dispensing box, the method comprising:

purchasing and receiving by a user of a glove dispensing box containing, fully surrounding, and enclosing a plurality of gloves therein and comprising a dispensing region thereof through which the gloves can be dispensed;

purchasing and receiving, by the user, of a glove singularizing accessory, the glove singularizing accessory being purchased and received by the user separately from said glove dispensing box, the singularizing accessory comprising an elongated and approximately rectangular frangible cover configured for attachment thereof to the glove dispensing box, the frangible cover comprising a linear longitudinal perforated slit and a linear transverse perforated slit that is perpendicular to the longitudinal perforated slit, wherein:

an intersection between the longitudinal perforated slit and the transverse perforated slit is located substantially at centers of both the longitudinal perforated slit and the transverse perforated slit;

a length of the longitudinal perforated slit is at least twice as long as a length of the transverse perforated slit;

both ends of the longitudinal perforated slit and both ends of the transverse perforated slit terminate in terminating holes that penetrate the frangible cover; and the longitudinal perforated slit and the transverse perforated slit are the only openings that are provided in the frangible cover;

directly attaching and fixing by the user of the frangible cover to the glove dispensing box, the longitudinal perforated slit and the transverse perforated slit being thereby located over the dispensing region of the glove dispensing box;

opening by the user of the longitudinal perforated slit and the transverse perforated slit;

reaching by the user's hand through the opened longitudinal perforated slit, the opened transverse perforated slit, and the dispensing region, and grasping by the user's hand of a selected one of the gloves within the glove dispensing box; and withdrawing by the users hand of the selected one of the gloves through the dispensing region, the opened longitudinal perforated slit, and the opened transverse perforated slit, while separated sides of the opened longitudinal perforated slit and the transverse perforated slit apply a frictional resistance that overcomes any mutual adherence between the plurality of gloves, so that any additional gloves of the plurality of gloves that may have become mutually adhered to the selected one of the plurality of gloves are scraped away and blocked from being withdrawn from the dispensing box.

11. The method of claim 10, wherein attaching and fixing by the user of the frangible cover to the glove dispensing box comprises causing an adhesive to adhere the frangible cover to the glove dispensing box.

12. The method of claim 10, wherein at least one elastic band extends between opposing sides of the frangible cover, and wherein attaching and fixing by the user of the frangible cover to the glove dispensing box comprises causing the at least one elastic band to surround the glove dispensing box.

13. The method of claim 10, wherein:

the glove singularizing accessory further comprises a layer of cover adhesive applied about a periphery of a downward facing side of the frangible cover, and a protective sheet removably applied to the layer of cover adhesive; and attaching and fixing by the user of the frangible cover to the glove dispensing box comprises removing the protective sheet from the layer of cover adhesive, thereby exposing the layer of cover adhesive so that it can be caused to adhere the frangible cover to the glove dispensing box.

\* \* \* \* \*